United States Patent
Leighton et al.

(10) Patent No.: US 11,632,125 B2
(45) Date of Patent: Apr. 18, 2023

(54) COMPRESSIVELY-ACCELERATED READ MAPPING FRAMEWORK FOR NEXT-GENERATION SEQUENCING

(71) Applicants: Bonnie Berger Leighton, Newtonville, MA (US); Deniz Yorukoglu, Cambridge, MA (US); Jian Peng, Cambridge, MA (US)

(72) Inventors: Bonnie Berger Leighton, Newtonville, MA (US); Deniz Yorukoglu, Cambridge, MA (US); Jian Peng, Cambridge, MA (US)

( * ) Notice: Subject to any disclaimer, the term of this patent is extended or adjusted under 35 U.S.C. 154(b) by 128 days.

(21) Appl. No.: 17/342,231

(22) Filed: Jun. 8, 2021

(65) Prior Publication Data

US 2021/0297090 A1    Sep. 23, 2021

Related U.S. Application Data

(63) Continuation of application No. 16/299,263, filed on Mar. 12, 2019, now Pat. No. 11,031,950, which is a continuation of application No. 14/837,567, filed on Aug. 27, 2015, now Pat. No. 10,230,390.

(51) Int. Cl.
  *G16B 30/00*     (2019.01)
  *H03M 7/30*      (2006.01)
  *G16B 50/50*     (2019.01)

(52) U.S. Cl.
  CPC ......... *H03M 7/3062* (2013.01); *G16B 30/00* (2019.02); *G16B 50/50* (2019.02)

(58) Field of Classification Search
  CPC ...... H03M 7/3062; G16B 30/00; G16B 50/50
  See application file for complete search history.

(56) References Cited

U.S. PATENT DOCUMENTS

| | | | |
|---|---|---|---|
| 10,242,155 B2 * | 3/2019 | Sanborn | G16B 20/10 |
| 2008/0077607 A1 * | 3/2008 | Gatawood | G06F 16/215 |
| 2012/0330566 A1 * | 12/2012 | Chaisson | G16B 30/10 |
| | | | 702/20 |
| 2013/0191351 A1 * | 7/2013 | Baym | G16B 50/00 |
| | | | 707/693 |
| 2016/0171153 A1 * | 6/2016 | Van Rooyen | G16B 30/00 |
| | | | 702/20 |

* cited by examiner

*Primary Examiner* — Syed H Hasan
(74) *Attorney, Agent, or Firm* — David H. Judson

(57) ABSTRACT

A method of compressive read mapping. A high-resolution homology table is created for the reference genomic sequence, preferably by mapping the reference to itself. Once the homology table is created, the reads are compressed to eliminate full or partial redundancies across reads in the dataset. Preferably, compression is achieved through self-mapping of the read dataset. Next, a coarse mapping from the compressed read data to the reference is performed. Each read link generated represents a cluster of substrings from one or more reads in the dataset and stores their differences from a locus in the reference. Preferably, read links are further expanded to obtain final mapping results through traversal of the homology table, and final mapping results are reported. As compared to prior techniques, substantial speed-up gains are achieved through the compressive read mapping technique due to efficient utilization of redundancy within read sequences as well as the reference.

7 Claims, 3 Drawing Sheets

COMPRESSIVELY-ACCELERATED READ MAPPING FRAMEWORK FOR NEXT-GENERATION SEQUENCING

BACKGROUND

Technical Field

This disclosure relates generally to next-generation sequencing (NGS) technologies and, in particular, technologies to store, transmit and process genomic data.

Background of the Related Art

Next generation sequencing (NGS) read data present challenges in data analysis and storage unrivalled in any other biological problem domain. Massive amounts of NGS reads (50-150 base pair fractions of genomic sequence) are generated every day by sequencing machines, growing annually at a greater exponential rate than computing power; these reads form the bulk of genomic sequences that must be stored and analyzed to obtain genomic information (e.g., GATK). Months of computing time are often required to process data for novel, large-scale sequencing studies that enable us to catalog human genetic variation, provide new insights into our evolutionary history, and promise to revolutionize the study of cell lineages in higher organisms. These computational challenges are at present a barrier to widespread use of NGS data throughout biotechnology, which impacts genomic medicine, environmental genomics, and the ability to detect signatures of selection within large sets of closely related read data.

A critical step in most sequence analysis pipelines is aligning, or mapping, the reads onto a reference genome to determine their loci in the genome. Read mapping is the costliest data processing step in sequence analysis pipelines. Existing read mapping methods (e.g., FM-index, hash table) require many sequence comparison steps, iterating over each read in order to map it onto reference genomes, which is expensive even when references are stored and organized efficiently. Thus, the time requirements of these known methods scale linearly with the size of the full read dataset, and each year require exponentially more runtime to process the exponentially-growing read data.

Identification of all possible mappings of a read within a given similarity threshold (denoted as "all-mapping") is of particular importance to many downstream analyses and is the most robust way to comprehensively analyze structural variants, transposons, copy-number variants, and other repeat elements within the genome. Even single nucleotide polymorphism (SNP) genotyping accuracy is shown to substantially improve through the use of multiply-mapped reads during SNP-calling. However, all-mapping is often not utilized by current sequence analysis pipelines due to its high computational cost when performed by existing alignment software.

The term "compressive genomics" describes compression of data in such a way that it can be searched efficiently and accurately without first being decompressed. Compressive genomics exploits the redundancy of genomic sequences to enable parsimonious storage and fast access. It has been demonstrated previously that search algorithms such as BLAST and BLAT could be adapted to run in a compressive genomics framework. A compressive genomics framework is useful for mapping NGS read data because it allows the search or mapping of each read to a compressed collection of similar genomes. While redundancy of reference genomes can currently be exploited in read mapping, these advances have not yet been applied to large NGS read datasets. One key to capitalizing on read redundancy is the observation that raw NGS read datasets, such as those from the Genome 10K and 1000 Genomes projects, are also redundant due to the high similarity across and within individuals' read data. This similarity, however, is not easy to mine.

Thus, to fully realize the conceptual advance of compressive genomics requires development of novel computational techniques that take advantage of this redundancy to compress large read datasets, as well as the reference, in such a way that they can be mapped without first being decompressed. The technique of this disclosure addresses this need.

BRIEF SUMMARY

This disclosure provides for a compressive framework, sometimes referred to herein for convenience as "CORA" (COmpressive Read-mapping Accelerator). The approach takes as input raw read datasets, maps the reads onto a reference (e.g., by boosting an existing mapper such as BWA or Bowtie2)) with compressive mapping technology, and outputs a file (e.g., a SAM file) with the resulting mapping that can be readily integrated into existing sequence analysis pipelines. The framework makes mapping of terabyte-sized read datasets tractable, achieving sublinear-time paired-end read mapping, which is already an order of magnitude faster than existing methods on NGS datasets. The approach is highly advantageous as it accelerates NGS read mapping, preferably by exploiting redundancy within read datasets.

Preferably, the acceleration provided by the technique relies on several aspects: (1) mapping reads onto other reads first, as opposed to mapping each read directly to the reference, to identify redundancy among reads; (2) mapping the reference to itself, preferably through a single preprocessing step, to create a comprehensive look-up table of similarities for fast retrieval; and (3) using a local neighborhood search (e.g., in the Hamming distance space of the self-mapped reference) to speed up sequence comparison. In one preferred embodiment, the CORA framework is comprised of combining these advances with an off-the-shelf mapper, applied before step (3).

For preprocessing, preferably the reference is mapped onto itself by building a high-resolution homology table of the reference genome sequence. The table stores the similarity information of all homologous or similar regions of a specified length in the reference genome, within a predefined Hamming distance. With this table, the framework can directly access all homologous or similar loci of any given locus, and thus are able to report all possible mapping locations at low computational cost, particularly useful for multi-reads (reads that map to multiple locations in the reference genome).

For the actual read mapping stages, preferably the approach first maps the reads to themselves to identify and compress similar substrings, with the goal of constructing a compressed representation of the read dataset. An off-the-shelf short-read mapper (e.g., BWA or Bowtie2) may then be used to coarsely map these clusters of compressed reads to the reference genome; these matches may be represented in the form of links, or pointers, to the homology table. Lastly, preferably these pointers to the homology table are followed to generate the final set of mappings through simultaneous traversal of the homology table and read links. In this manner, the approach is able to identify all high-quality alignment positions in the reference with nearly perfect sensitivity.

The foregoing has outlined some of the more pertinent features of the disclosed subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION

For descriptive purposes, the framework and technique of this disclosure is referred to as "CORA" (COmpressive Read-mapping Accelerator"), but this nomenclature is not intended to be limiting. Typically, the tool is implemented as computer software executing in one or more hardware processors. The computer software may be implemented as one or more programs, processes, instruction sets, execution threads, scripts, or the like.

Figure 1:
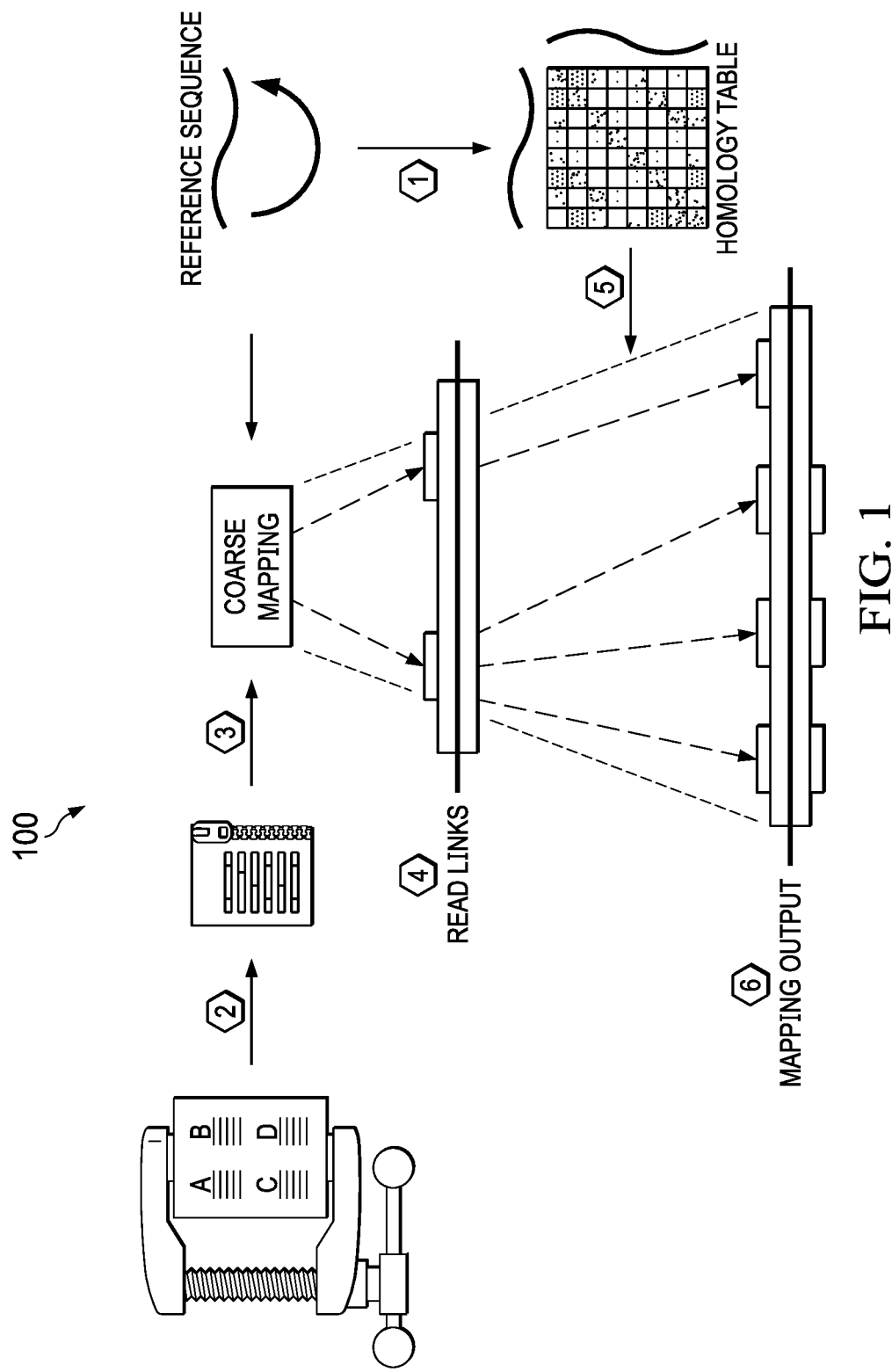
FIG. 1 depicts the compressively-accelerated read mapping technique of this disclosure.

Compressively-accelerated read mapping according to this disclosure addresses the inefficiencies of mapping high-throughput NGS reads by capitalizing on redundancy within both read datasets and the reference. The basic technique is shown in FIG. 1.

As a preprocessing step (1), a high-resolution homology table 100 is created for the reference sequence 102 by mapping the reference to itself. The homology table preferably contains all homologous pairs of loci in the reference above a similarity threshold, allowing direct access between similar locations in the reference during mapping. Once the homology table is created, the first step (shown as (2)) in compressive read-mapping then is to compress the reads to eliminate full or partial redundancies across reads in the dataset. Preferably, compression is achieved through self-mapping of the read dataset. Next, an off-the-shelf aligner (or its equivalent) can be used to perform a coarse mapping (shown as (3)) from the compressed read data—clusters of similar substrings—to the reference. Each read link (at (4)) represents a cluster of substrings from one or more reads in the dataset and stores their differences from a locus in the reference. Read links are further expanded to obtain final mapping results through traversal of the homology table (at (5)), and final mapping results are reported (at (6)). Substantial speed-up gains are achieved through compressive read mapping due to efficient utilization of redundancy within read sequences as well as the reference.

Within the CORA framework, the coarse mapping stage identifies substrings (or k-mers) within reads that are similar to a location in the reference, producing read links. These read links can be inexact; thus even when there are no exact matches for a k-mer, the coarse-mapping stage will produce inexact matches, enabling the mapping inference stage of CORA to capture homologous loci to the link through traversal of the homology table.

The following provides additional details regarding the framework.

Homology Table Construction

Before performing compressive read mapping, the approach first preprocesses the homology table, a high-resolution all-to-all similarity map of the reference genome onto itself, as well as the associated reference index for each locus to be used in later read mapping. For CORA's k-mer based compressive read mapping, a homology table that represents all homologies in the reference, exact as well as inexact, is very useful, as it enables fast retrieval of additional mappings of a k-mer once one mapping is identified in the coarse-mapping stage. In one embodiment, and for a chosen homology block length (e.g., 32-64 base pairs) and similarity measures (e.g., Hamming distances 0-3), the homology table of a reference genome contains links between all homologous loci satisfying the length and similarity requirements. In other words, instead of representing the sequences of k-mers in a given reference genome, a homology table represents pointers for each position in the genome indicating all of its neighboring k-mers. As such, the homology links form an inter-web of similar loci within the reference genome to be used in conjunction with the compressively accelerated read mapping technique of this disclosure. Both homology table and reference index need only be computed once for a given reference genome, after which they can be repeatedly used for further compressive mapping runs on the same reference genome.

More formally, given a reference DNA sequence R, a substring length k, and a mismatch error threshold s, a homology table $H(R, k, s)$ is a compact data structure that stores the links among all similar k-base substrings (k-mers) of R (up to s mismatches), under reverse complementation. The term k-mer typically refers to all the possible substrings, of length k, that are contained in a string. In computational genomics, k-mers refer to all the possible subsequences (of length k) from a read obtained through DNA sequencing. To efficiently construct the homology table H, preferably an exact homology table $HE(R, k)$ that stores the links among all identical k-mer occurrences in the reference under reverse complementation is built. Based on this exact homology table, an inexact homology table $HI(R, k, s)$ that stores the homology links among k-mers with at least one and at most s mismatches is built. Together, the exact homology table $HE(R, k)$ and the inexact homology table $HI(R, k, s)$ form $H(R, k, s)$. In other words, instead of storing neighborhood information for all positions in the genome, CORA compactly represents the neighborhood information between sets of positions with identical k-mers.

Preferably, these tables are generated, organized and stored separately to optimize runtime performance and memory/disk usage. Although the technique describe below refers to a substitution-only version of the inexact homology table, it is straightforward to extend homology tables for other types of edits as well, such as indels.

Exact Homology Table

Preferably, an unordered hash table is used to construct the exact homology table. For each k-mer, one preferred approach uses its sequence as the key and its first occurring position in the reference genome as the value in the hash table. If the k-mer appears in other position(s) in the reference, an equivalence class is created to store all such positions. Each equivalence class is stored as a list of genomic positions and their directions with respect to the representative, which allows a quadratic number of exact homology links between pairs of genomic loci to be stored within linear space. Preferably, this representation is further compacted by collapsing adjacent concordant equivalence classes. If there are two or more adjacent concordant equivalence classes (all loci within an equivalence class is shifted by one position with respect to another equivalence class), preferably they are merged in a way that only the values of the first equivalence class with the smallest representative position are kept, with an additional block-length value, which indicates how many adjacent concordant equivalence classes are collapsed into a single one.

A formal definition of the exact homology table block merging can be given as follows: Denote $e_i=(c_i, p_i, d_i)$ as members of the equivalence class E, for i ranging from 0 to $|E|-1$, $c_i$ representing the chromosome ID of the $i^{th}$ element, $p_i$ being a positive integer representing the chromosome position of the $i^{th}$ element, and $d_i$ being either 1 or −1, respectively representing the forward or reverse complement direction of the homology of the $i^{th}$ element, with respect to the representative element $e_0$. The representative element is required to always have forward direction ($d_0=1$). Two equivalence classes E and F is merged to create a new equivalence class $E_2$ of block length 2 if and only if $|E|=|F|$ and for all $e_i=(c_i, p_i, d_i)$ within E, there exist an $fj=(c_j, p_j, d_j)$ within F, such that $c_i=d_i=d_j$, and $p_j=p_i+(d_i\times d_i)$. Blocks of length longer than 2 can be inductively defined: If E and F can be merged, F and G can be merged, then E, F, G can altogether be merged into E3, an equivalence class with a block length of 3. Merging operation for block lengths larger than 3 can be similarly defined.

Depending on the size of the data (the genome), a single hash table representing all distinct k-mers of size ~50 bp within the reference genome may be impractical. For this reason, a multi-pass homology table construction approach may be used and, in particular, by storing only a subset of the k-mers in the hash-table in each pass to optimize the empirical performance and memory usage. The multi-pass construction of the homology table is simply a way to reduce the memory requirements by trading against run-time. Given unlimited memory, equivalence classes for all k-mers would be computed in a single pass, generating the homology table. However, for a large reference genome (e.g. human), and as noted, preferably the framework divides the space of k-mers into smaller subsets and does a pass for each subset, reducing memory needed for each pass, and then combining the passes together at the end.

Further details regarding the exact homology table construction are now described. As described, the representation may be further compacted by collapsing adjacent concordant equivalence classes, requiring the size of the equivalence classes to be equal and each item in the class to be adjacent to the corresponding item in the correct direction. For example, an equivalence class [15: 35+, 73−, 112−] can be merged with [16: 36+, 72−, 111−], whereas not with [16: 36+74−113−]. Here 15 and 16 are the representative positions, and other values represent other positions in the reference with the same k-mer in forward (+) or reverse complement (−) directions. If there are two or more adjacent concordant equivalence classes, preferably they are merged in a way that only the values of the first equivalence class with the smallest representative position are kept, with an additional block-length value, which indicates how many adjacent concordant equivalence classes are collapsed into a single one.

As noted, the multi-pass homology table construction as described above preferably works by storing only a subset of the k-mers in the hash-table in each pass. For instance, k-mers that start with A and end with G (in the form [A . . . G]) should be processed in the same pass with the reverse complement form [C . . . T]. For these k-mers, construct a hash table AG. In this way, the whole table is constructed with 10 passes. Specifically, these 10 passes include 1) AA and TT, 2) AC and GT, 3) AG and CT, 4) AT, 5) CA and TG, 6) CC and GG, 7) CG, 8) GA and TC, 9) GC, and 10) TA. These 10 passes were designed to optimize the empirical performance and memory usage. By using more nucleotides from both ends of k-mers, it is possible to store the hash-table using even smaller memory size during each pass. In our implementation, we used the above mentioned 10-pass approach.

Inexact Homology Table

Generating the inexact homology table, HI(R, k, s), which represents all-to-all homologies of k-length substrings in R with between 1 and s mismatch errors involves a similar but more sophisticated approach. To generate the inexact homology table HI(R, k, s), preferably the approach uses the exact homology table HE(R, k), particularly the pre-computed equivalence classes, to reduce computation and storage requirements. Instead of constructing the inexact homologies between substrings on the reference, preferably the approach does so among the equivalence class representatives in the exact homology table HE(R, k). The remainder can be inferred directly using the equivalence class members. Preferably, the inexact matches between equivalence class representatives are identified by a seed-and-extend algorithm, which first checks if there is an exact match between seeds on two given k-mers, and then extends the remaining bases of the k-mer sequences to identify any mismatches. A spaced-seeding scheme may be used for performance and parallelization purposes. To that end, and instead of selecting seed positions from a single consecutive fragment of the k-mer, seeds that are spaced out with equal-sized gaps between each included position are selected. Furthermore, preferably the set of seed positions is closed under reverse complementation, with positions symmetrically selected from both ends of the k-mer.

To construct HI(R, k, s) for a given R, k and s, s+1 auxiliary hash tables are constructed, each corresponding to one of s+1 seeds extracted from equivalence classes from the exact homology table. Preferably, the seeds are sampled according to the position selection scheme described above. In the hash table, preferably the binary representation of a seed is used as the key, and the list of positions in the reference that contain the seed sequence is used as the value. When a hit is found, the current k-mer position in the reference is added to the list of the corresponding key. Similar to the exact homology table creation, due to the large size of the human reference genome, storing all hash tables representing each k-mer would require a large amount of memory. For this reason, preferably a multi-pass approach similar to the one used for the exact homology table and parallelized is used for this stage, as different seeds do not affect each other.

The representation of the inexact homology table may be further compacted by merging any adjacent pairs of inexact matches with consecutive mismatch positions in the alignment directions.

The following provides further details regarding the construction of the inexact homology table. As noted, preferably seed positions are chosen to be closed under reverse complementation for two reasons. First, it allows reverse complement of a seed to correspond to the exact same positions in the k-mer, so that there is only a need to store the lexicographically smaller direction of any seed in the hash table, and thus need only to search each seed once in the hash table. Second, this choice allows simple parallelization and a multi-pass implementation of the hash table, because data splitting can be performed easily. As DNA sequences are highly locally repetitive, some bins in a hash table can get very large for frequently-occurring seeds; the spaced seeding scheme also is more efficient, as the chance of two seeds being identical is reduced.

As an example, the inexact homology table for hg19 reference genome is constructed with a 10-pass approach with interleaved 24-split parallelization on 12 hyper-threaded processors. (Note that this is still 10 passes but 24× parallelized for each pass.) For parallelization of split signals, two bases from the ends of each seed are used, which gives 144 reverse complement agnostic sets—as opposed to 10 for one base from each end. These are collected into 24 balanced-set groups. The balancing is accomplished according to the general human GC ratio assumption (2*IA or TI=3*IC or GI). These 24-set groups are used to do a 24-pass for the collapsing stage of CORA when running whole genome datasets.

The concordance of two inexact homologies are defined in terms of their relative position to each other as well as the relative positions of the edits within each inexact homology. For example, an inexact homology from x to y with an edit at position n is concordant to another inexact homology from x+1 to y+1 with an edit at position n−1, and similarly from x+k to y+k with an edit at position at position n-k (for 0<k<n). The compressed inexact homology table represents all n of these homologies as a single homology block of size n, from x to y with an edit at position n.

For generation of exact and inexact homology tables, CORA preferably allows user-specified multi-pass counts as the number of processes to be used for parallelizing each pass as well as the user-specified split signals for balancing processor load during parallelization.

Figure 2:
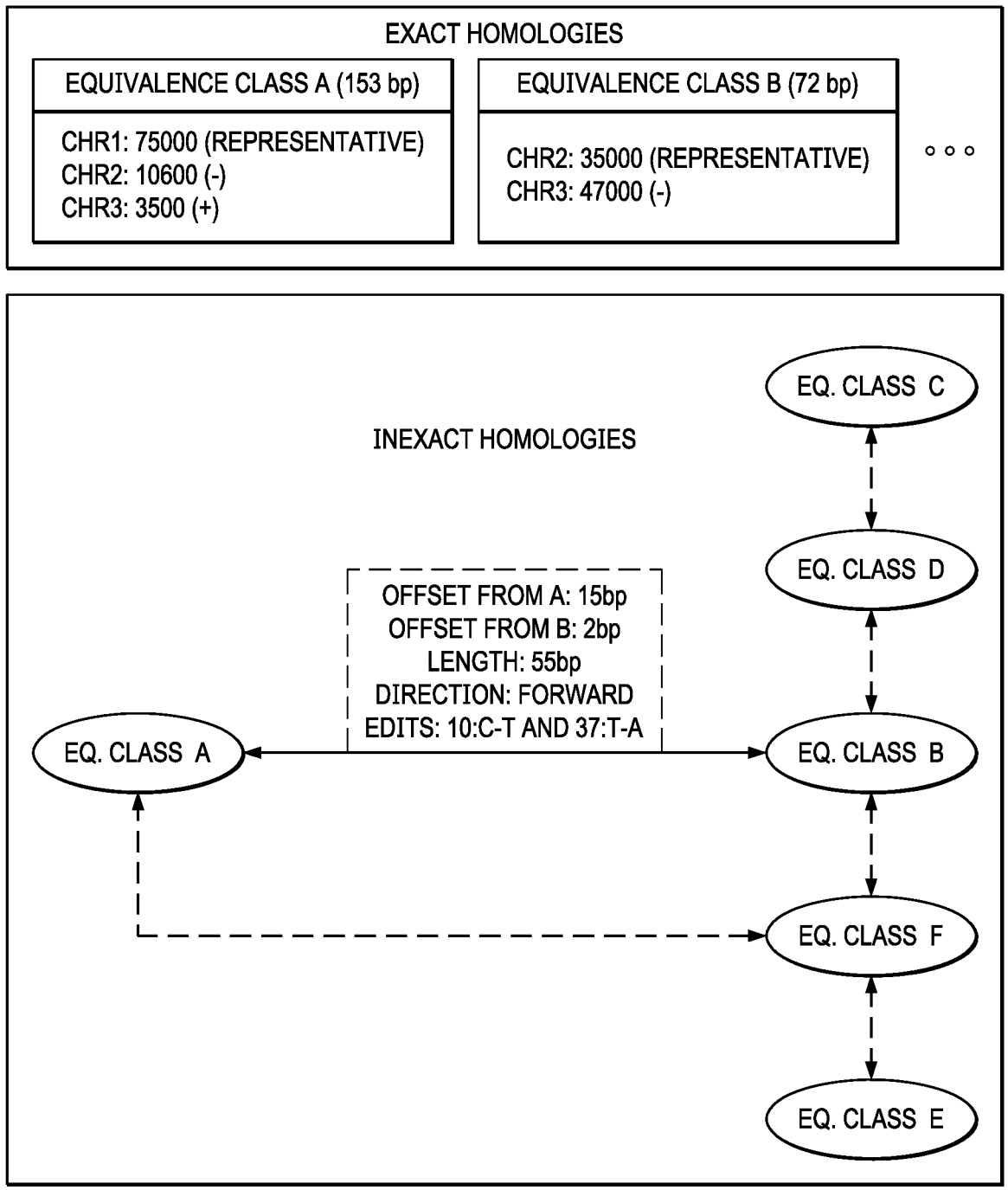
FIG. 2 depicts a compact representation of the homology table with exact and inexact homologies in a representative embodiment.

FIG. 2 depicts a compact representation of the homology table with exact and inexact homologies in a representative embodiment;

Compression of Read Data

In this phase of the CORA framework, the main goal is to reduce the redundant information within and among reads in a large NGS dataset, achieving a compact representation of the reads in the form of links to the reference; these represent a position in the reference genome similar to a substring within the read and its differences. This representation of reads allows faster sequence matching as we need only check corresponding edits rather than performing expensive sequence comparisons.

The two main stages of the links table construction are (1) collapsing and (2) coarse mapping, each of which is now described.

Collapsing

The collapsing stage aims to eliminate any direct redundancy within and among reads in NGS datasets. For relatively short single-end reads (~35-75 bp), this stage preferably involves identification of all identical reads (under reverse complementation) and collapsing them into unique reads with compact names that encode the original read order in the input (e.g., fasta/fastq) file. As sequencing error rates of recent Illumina machines are roughly 1-2%, the probability of a read containing a sequencing error by chance is considerably high when its length is greater than 75 base pairs (~50-80%). Because most sequencing errors are clustered within low-quality reads, however, a large portion of reads are sequenced perfectly, without any sequencing errors, for relatively short reads.

To improve the collapsing performance of longer NGS reads (~76-150 bp), the CORA framework preferably employs a split collapsing scheme wherein each read is first split into two shorter consecutive substrings of the same length; the splits are then collapsed individually and processed. Later, in the final phase of CORA, the consecutive splits are identified and merged into whole reads again.

In the collapsing stage, the CORA framework preferably also adds all unique read-mers, k-mers with the size of a split, from the reference genome to the hash table. This action allows very fast identification of all read sequences and splits that perfectly match to a position on the reference genome, resulting in substantial runtime savings within the "coarse" read mapping stage.

For mates of a paired-end read and splits of a mate to be identified, CORA preferably assigns corresponding IDs to the splits and mates of the same read. These ID values preferably are encoded using a range of text-readable ASCII characters from '!' to '~' (with an alphabet size of 94), allowing off-the-shelf mappers to readily parse the read name format without any modifications and directly operate on CORA's compact read representation.

The length of each sequence ID in the collapsed dataset typically is determined by the total number of reads to be mapped in a single mapping task. CORA's compact encoding scheme allows each read in a dataset consisting of ~19.5 million paired-end reads to be uniquely identified with 4 character sequence IDs, ~1.8 billion paired-end reads with 5 characters, and ~172 billion paired-end reads with only 6 characters. Because the sequence IDs preferably are assigned the same ordering as they are listed in the input (fasta/fastq) files, the original read and sample information can also be easily retrieved.

Preferably, the framework implements read collapsing with an unordered hash table (e.g., unordered_map class in C++ standard library), consisting of DNA sequences (the lexicographically smaller of the forward sequence or its reverse complement) as hash keys and a string that represents the encoded collapsed read names as the value for each key. For large datasets with many unique sequences that would cause the hash table to exceed the memory limit, a multi-pass approach is used to keep the size of the hash table within specified memory bounds.

To improve read collapsing performance of longer NGS reads (>70 bp), or paired-end reads CORA framework, instead of compressing the entire read sequence, the framework may split the (paired-end) read into shorter k-mers of the same length (between 33-60 base pairs) and collapse them as independent sequences even if they originate from the same read sequence, producing a set of non-redundant k-mers. This collapsing stage is applied prior to coarse-mapping stage and therefore the subsequent coarse-mapping step is performed in a read agnostic manner (i.e without the knowledge of which k-mer sequences come from which reads). For mates of a paired-end read and k-mers of a read to be identified post-coarse-mapping, CORA assigns corresponding IDs to the splits and mates of the same read. Only after coarse-mapping stage, these collapsed k-mers are reorganized based on their IDs and merged into whole reads in order to produce the final mapping results. As a tool that can rapidly identify the positions of homologous k-mers in the reference, the homology table precisely complements the k-mer based compression of reads, together creating a very efficient method for NGS read mapping for large datasets with high redundancy.

Optionally, through the use of a database of k-mers in the reference, CORA can also identify exact k-mer matches to the reference during collapsing and print them to a different output together with the chromosome and position information of the reference k-mer match, further reducing the number of non-redundant k-mers to be processed in the coarse-mapping stage. This optional feature is enabled in the experimental results presented in the paper.

Apart from compressive power (and compressive-mapping speed) gained from k-mer based read compression, the flexibility of collapsing independently chosen k-mers within the read rather than the read itself enables a number of additional features for CORA framework. As the k-mer length is independent from the read-length, reads with different lengths can be processed together in the same compressive mapping run. This also allows, dynamic trimming of low quality of reads on-the-fly during mapping, which even further facilitates compression reducing lower redundancy parts of the reads. One caveat to this is selecting overlapping k-mers, which reduces the maximum mapping distance that can be detected if there are variants or sequencing errors in the overlapped region in the read. An alternative to this would be to always pick non-overlapping k-mer from the reads, but leave a small number of bases in the read that are not covered by k-mers, which can be checked during mapping inference stage in order to verify whether the mapping similarity requirements are satisfied when considering the uncovered bases.

Selecting fewer but longer k-mers results in lower compression in the collapsing stage thus increases the time spent on coarse-mapping, yet decreases the average number of neighbors each reference locus has in the homology table, enabling faster homology table traversal. Whereas selecting many but shorter k-mers results in higher compression during collapsing and less time spent on coarse-mapping, but increases the number of homologies in the homology table as well as time spent on homology table traversal.

Coarse Mapping

Coarse mapping is the stage in which the CORA framework preferably utilizes the short-read mapping capabilities of an off-the-shelf mapper. Any read mapping tool that can report a best mapping (i.e., a mapping with a minimum Hamming or Levenshtein (edit) distance among all possible mappings of a read), such as BWA or Bowtie2, can be directly adapted to the CORA framework for this purpose. For off-the-shelf aligners that do not allow a best-mapping scheme, alternative strategies can be designed for integration with some caveats. In particular, if a mapper does not allow best-mapping but allows a user-specified limit on the number of reported mappings, a mapping mode that reports only a single mapping (not necessarily with minimum error) can be integrated into CORA, with minor loss in final read-mapping accuracy. If the off-the-shelf mapper provides user-specified limits on the number of errors within a read, it is also possible to perform an iterative re-alignment scheme, at each stage aligning previously unmapped reads with a higher error threshold. While this approach will preserve final read-mapping accuracy, it will yield less compressive acceleration due to the heavy cost of re-alignments within the coarse mapping stage.

Unlike most read mappers, CORA's coarse mapping stage preferably does not aim to find actual mapping locations of each read (which would ultimately provide little compressive acceleration), but instead identifies a good "representative" position in the reference that a read or a split can be mapped to and be represented in the form of compact links (i.e. position and differences). For short k-mer sequences that are used within the coarse-mapping stage, it is substantially faster to find a single good location in the reference than find all mappings within the substitution-error neighborhood. There may be more than one good location.

For paired-end mapping, finding a proper mapping in the reference involves finding multiple good locations for each mate and merging them according to the user-defined allowable interval of insert size between the mates (e.g. 150-650 bp). Coarse mapping for a paired-end read typically consists of merely finding a good location in the reference for each mate independently. Similarly, for longer reads that are divided into two splits, finding a coarse mapping would require only finding independent locations in the genome for each split.

Through these conceptual advances in the mapping stage, the CORA framework achieves massive speed gains (typically more than an order of magnitude for all-mapping and more than twice for best-mapping), as compared to the original performance of the off-the-shelf mappers.

Constructing the links table from the coarse mapping output generated by the off-the-shelf mapper (preferably in SAM format) involves simply scanning the SAM file and creating a link item for the read code on each line. Each link in the table preferably contains the read name encoding described above, the position in the reference, as well as a list of mismatch offset positions from the beginning of the read together with its nucleotide change in the read. Due to the fact that the links table preferably contains the differences of each read/split from the reference, it is possible to regenerate the original read sequences in the input, and thus compression of read data within the CORA framework is lossless.

Homology Table Traversal

The main goal of this phase is to infer final paired-end read mapping results, making use of the pre-computed homology table of the reference, as well as the compact links table representing the read dataset.

As links and homology tables preferably are all represented in terms of position in the reference and the differences from it, rather than the read sequence itself, almost all of the computation in this phase of the CORA framework is performed in terms of edit operations rather than direct sequence comparison. Because a link generally has much fewer edits than the number of bases in the read, utilizing algebraic relations within this "edit space" is desirable as it results in a much more efficient sequence comparison method than the base-to-base comparison approach used in conventional read mapping.

Figure 3:
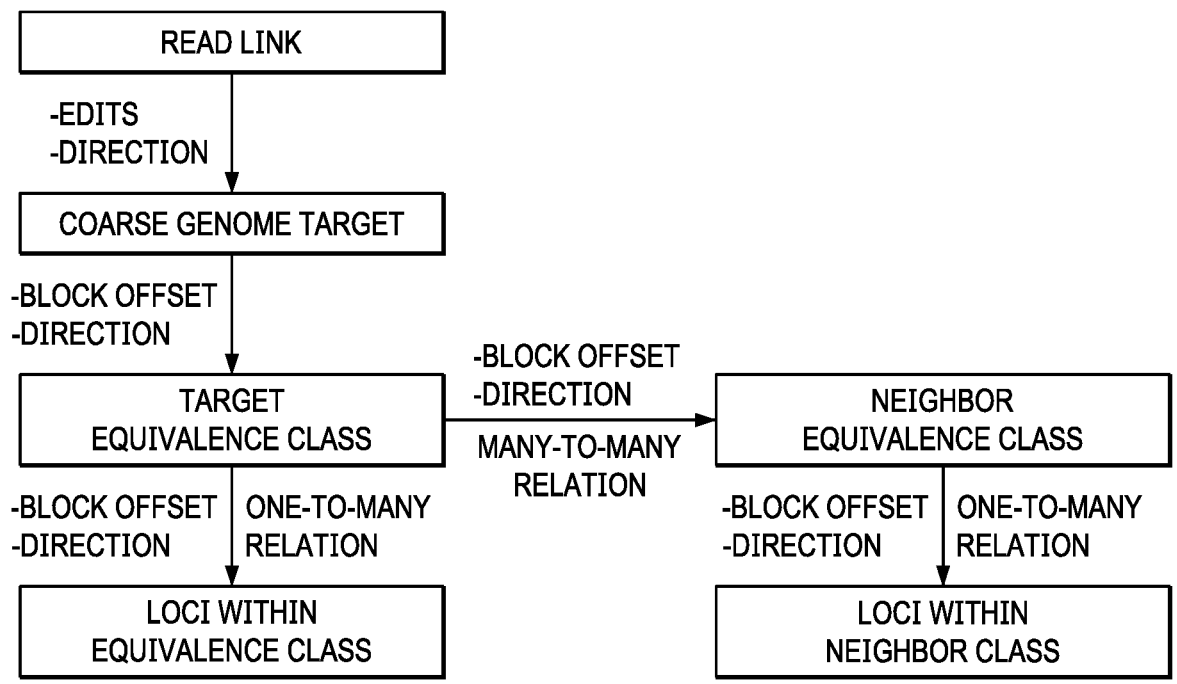
FIG. 3 illustrates the homology table traversal scheme of the framework according to the techniques of this disclosure.

A schematic representation of the homology table traversal for a single read link is provided in FIG. 3. As depicted, each link connects one or more reads (or splits) to a position in the reference (the anchor of the link) in forward or reverse complement direction, indicating homology within a small number of edits. Typically, this anchor either is a unique read-length k-mer in the reference genome or associated with an equivalence class within the exact homology table. In the latter case, the anchor is linked to the equivalence class in the forward or reverse complement direction, with a block offset value indicating the starting location (say offset=p) of a substring of the equivalence class representative that is identical to the anchor sequence. If an anchor does not belong to any equivalence class, it is considered to be the representative of its own equivalence class.

A representative of an equivalence class points to all members of the equivalence class for each valid offset (until the end of the block) in forward or reverse complement direction. Among these pointers, preferably only the ones with the offset p are relevant to the read link and only for these will the inferred mapping result be reported. Furthermore, the equivalence class representative of the anchor can be linked to other class representatives through the inexact homology table. Each of these pointers contains the direction of homology (forward or reverse complementary), block offset in the compressed inexact homology block representation, and the edit script to convert one k-mer to another. Provided that the juxtaposition of the edits from read link to the anchor and from the anchor's class representative to the neighboring equivalence class still contains less than or equal to the Hamming distance threshold, read mappings associated with all members of this neighbor equivalence class will be reported.

For short single-end reads (e.g. <75 bp) that are collapsed as a whole read into read links, the final mapping output can be generated by the procedure described above. For paired-end and longer reads, which are divided into two splits (e.g. >75 bp), all links relevant to the read (up to four links) are traversed to generate the final mapping(s). CORA achieves this traversal preferably by loading the links table in multiple passes to avoid exceeding the memory limit. These links are then independently converted into mappings of the read mate or the split. In the end, these mappings are merged to generate the final set of paired-end mappings.

Although the links table is a lossless representation of the read sequences in the original dataset, as inexact homologies within an error bound are not transitive, a very small portion of the read or split mappings can be missed initially at the error neighborhood boundary (less than 2% in tested NGS datasets). Moreover, for long single-end or paired-end reads, among the splits of a read, if most of the errors fall within only one of the splits, the coarse mapping stage may not be able to capture the mappings of the split with multiple errors. The mapping of the full read thus will not be reconstructed from homology table traversal alone. To ameliorate the sensitivity loss that can arise from either of these issues, CORA preferably employs an efficient recovery scheme to identify such missed split mappings. Provided that only one of the splits in a paired-end read is missing, a nucleotide-level string comparison is made between the original sequence of the missing split and the sequence at the corresponding position in the reference genome. This recovery approach substantially reduces the sensitivity loss (down to <0.2% in tested NGS datasets), resulting in a very accurate compressive alignment scheme with substantial runtime speed-up.

For further speed optimization on high-coverage read datasets, CORA preferably uses a link memoization scheme. In particular, it saves the inferred genomic positions for links that represent more than a set threshold of reads (or splits) so that the homology table is traversed only once for the link. In whole genome real-data experiments, this threshold is chosen to be 20, which gives a good balance between runtime improvement and additional memory required for memoization.

Further Implementation Details

The CORA framework is implemented in any suitable computing language, e.g., the C++ programming language. As has been described, the framework does not have any dependencies apart from the user-specified coarse mapping tool to be incorporated. Thus, virtually all short-read mapping tools can be plugged into the CORA framework with minimal or no changes to the implementation. Such tools and mapping modes include BWA, Bowtie, and Bowtie2. One implementation of CORA can perform mappings of paired-end read datasets with uniform read-lengths (between 2×36 bp and 2×150 bp) within a Hamming distance threshold. In addition, users can specify an allowable insert length interval for mate-pairs. CORA performs end-to-end mapping of reads that corresponds to the global alignment of reads to a locus in the reference. In one implementation, CORA does not make use of quality scores within the alignment (all substitutions have equal weight within the Hamming distance metric); however, quality scores can be recovered using unique IDs assigned to reads in the sorted order of the original read dataset.

For easy integration of other mapping tools into the CORA framework, a manual coarse mapping mode preferably is used. In this approach, users can give a series of commands to run for the coarse mapping stage of CORA (specifying the executable files, input, output and reference), and CORA automatically calls these commands to perform the coarse mapping stage, without requiring any code changes in the mapper or CORA framework.

As noted CORA allows the user to specify printing all-mappings, best-mapping, unique-mappings or best stratum mappings, which correspond to printing all mappings within the highest tier.

As homology tables constructed with larger Hamming distances are both more inefficient and more memory intensive, it may be desirable to construct the homology table with a smaller Hamming distance, sacrificing a small percentage of sensitivity for improved performance.

When constructing the homology table, a good trade-off for the size of the table and the sensitivity of the mapping results can be achieved with a homology table constructed with distance N instead of 2N. Even though this partial homology table allows reconstruction of only >98% of all k-mer mappings to the reference, CORA's recovery scheme during its traversal of the homology table can recover most of such missed mappings. As described, this recovery scheme utilizes other k-mers within the read as anchors, empirically increasing the sensitivity of CORA to >99.7% in the final mapping results. The recovery scheme thus enables more sensitive mapping than the homology table with Hamming distance of N can provide on its own.

Variants and Extensions

Many variants may be implemented within the scope of this disclosure. For example, the framework may support indels and soft clipping for long reads with low-quality regions. Though the collapsing and coarse mapping stages of the CORA framework can already accommodate indels during read alignment (assuming the coarse mapper used can report mapping results with indels); for accurate compressive alignment, the homology table may be augmented with inexact homology links containing insertions and deletions. Soft-clipping of reads (e.g. trimming off the low quality end of a read) can be supported by CORA with an approach similar to the recovery scheme described in the mapping inference stage, given that a non-trimmed read-mer within the read is still present in the links table. In addition, greater flexibility with a user-defined Hamming distance may be implemented. Further, the framework may be extended to add support for multi-reference alignment by augmenting the homology table with links to individuals' variants within user-specified VCF (Variant Call Format) files.

To perform read-mapping with indels, the coarse-mapping method used must handle indels. To perform this upgrade to CORA, the mapping inference stage is modified to expand the "edit space" of read links from substitutions to also insertions and deletions. The substitution-only homology table is still maintained for traversing the homologies in the reference. CORA may also be used to perform sensitive read-mapping with indels using a substitution-only homology table.

Even though the homology table data structure is built using a Hamming distance metric that only allows substitutions, it is possible to report gapped final mappings with indels (insertions and deletions) given that the coarse-mapping is performed using an off-the-shelf tool that can perform gapped mapping and the error penalty assigned to insertions and deletions is larger than or equal to the penalty assigned to substitutions (e.g. Levenshtein distance that assigns identical penalties for substitutions, insertions, and deletions).

In one embodiment, the homology table is built to provide Hamming neighbors of a k-mer in the reference for a fixed error distance threshold, E. However, it is also possible to recover homologies of (k–e)-mers in the reference (s<E), guaranteed to discover all homologies within a Hamming error distance threshold of E–e, ignoring the matches/mismatches at the last e bases of homology table k-mers. Since e is often much smaller than k, most of the E-distance homologies of (k–e)-mers will also be recovered. This ability to search for (k–e)-mers in the homology table enables neighborhood search of k-mers that are coarse-mapped with an insertion in them. In the case that a k-mer is coarse-mapped with a single base insertion in the k-mer link (which corresponds to a single base deletion from the reference), the k-mer is aligned to a (k–1)-mer in the reference. Using the approach above, CORA can recover most of the homologous regions of the (k–1)-mer.

In the case of a single nucleotide deletion in the k-mer link (insertion in the reference), the k-mer corresponds to a (k+1)-mer in the reference. In this case, the homology table can enumerate the k-mer homologies that are contained within this (k+1)-mer and then determine whether the (k+1)-mer homology is within the valid error distance threshold by checking the similarity of the last base in the (k+1)-mer.

In the case of multiple insertions and deletions in the k-mer link, the homology table traversal strategy is determined by t=#deletions−#insertions. If the t<0, the first strategy is employed that ignores the last t bases in the k-mer homologies; if t>0, the second strategy is employed that checks for t additional bases at the end. If t=0, the original version of the k-mer based homology table traversal is performed, with the only difference of handling shifted bases due to insertions and deletions within the k-mer when juxtaposing k-mer homology edits with the edits from the k-mer link. The t value is also important when merging multiple k-mer link mappings into a whole read during the final mapping. If one of these k-mers have a positive or negative t value, k-mer merging is performed between accordingly adjusted mapping positions.

Due to the way homology table is constructed, some of the k-mer mappings to the reference within the given Hamming or Levenshtein distance are to be lost. As described above, a recovery scheme CORA employs to recover these missed mappings may be implemented. Further details of that recovery scheme are now described.

By way of background, although the links table is a lossless representation of the read sequences in the original dataset, there are a three main reasons why a read mapping can be missed during the standard traversal of the homology table. These are: (a) using an inexact homology table with a distance threshold lower than twice the mapping error, (b) loss of sensitivity during coarse mapping, and (c) non-uniform distribution of errors among k-mers sampled from the read during collapsing. In order to achieve near-perfect sensitivity, CORA employs a recovery scheme that handles unmapped k-mers scheme that addresses (a-b) and missing homology recovery scheme handling (c).

To recover mapping locations of reads with unmapped k-mers, CORA preferably keeps track of all k-mers that are unmapped during the coarse-mapping stage. Once the homology table traversal generates all mapping loci for the other k-mers of the read, if more than a certain percentage (e.g. 75%) of k-mers of a read constitute a viable mapping that is only missing the unmapped k-mers but satisfy the error distance and min/max read insert length conditions, the unmapped k-mer is extended using a base-by-base comparison method (or banded dynamic programming for edit distance alignment to recover indels).

When constructing a homology table, to guarantee perfect sensitivity for obtaining all matches of a k-mer in the reference genome within a Hamming distance of D, the homology table should ideally use a distance threshold of 2D. This is due to the fact that, even when a read k-mer is within distance D to both coarse mapping locus and the final mapping locus, the distance between the final mapping locus and the coarse mapping locus could as large as 2D. However, as homology tables with large error rates take substantially longer to construct and consume larger memory, for practical performance reasons, the threshold of the homology table can be chosen to be less than 2D (such as D, which is used for the main experimental results in the paper), resulting in imperfect sensitivity. In order to recover these mappings that have distance higher than D to the coarse mapping, CORA again employs a nucleotide-level string comparison given that a large percentage of the remaining k-mers constitute a viable mapping.

For further speed optimization on high-coverage read datasets, CORA preferably uses a memoization scheme. For the read links represent more than a certain number of k-mers in compressed form, CORA traverses the homology table once and saves the inferred genomic positions for the link in a lookup table. Then for each of the k-mers within the link, this lookup table is used instead of re-computing the genomic neighbors using the homology table.

Similar to homology table construction, read-compression stage can also be performed in arbitrarily small multi-pass runs. As noted, preferably the coarse-mapping stage within CORA involves running an off-the-shelf tool with no modification to its code. Thus, the memory used in this stage is directly dependent on the memory profile of the coarse-mapper. A user-specified coarse-mapping memory option enables a user to manually specify the memory limit to the coarse-mappers.

The mapping inference stage of CORA has the most varied memory usage profile, highly dependent on the type of mapping method used and the performance options. Because CORA can also perform a multi-pass computation over the read links, the minimum memory requirement of this stage is not dependent on how large the read dataset is. Because CORA preferably reports final mapping results through traversal of the homology tables, it needs to fully store the homology tables in memory as well as the reference genome.

For a fast best-mapping mode, the inexact homology table is skipped; thus the remaining data structure can fit into 10

GB of memory. However, for CORA's all-mapping mode and sensitive best-mapping mode, both exact and inexact homology tables are stored in memory, requiring around ~50 GB of memory.

Further acceleration of CORA through memoization of homology table traversal results for common k-mers, which uses additional memory for faster computation of mapping outputs. Even though CORA's memory usage is higher than existing methods, the cost of memory is getting exponentially cheaper (currently ~5-8$ per GB) and therefore a genomics computing node that can run CORA can be obtained for relatively low cost. The benefits from CORA's runtime savings as well as the additional sensitivity, and thus statistical power gained through its mapping, outweigh the cost of its memory use.

Further memory optimizations for CORA's homology table representation may be implemented, allowing it to be compressed further. Another potential optimization is to represent the homology table in a layered structure, where only commonly accessed homologies are stored in memory and the remainder is stored on disk.

The homology table data structure may be augmented to be more flexible and able to answer queries for various k-mer lengths. Such an augmentation of the homology table would make the index more robust and allow the use of the same index for different types of sequencing datasets. A service provider may host homology tables of common reference genomes for a variety of k-mer lengths, enabling users of CORA to perform experiments on a variety of datasets without needing to generate the index.

The techniques of this disclosure provide significant advantages.

CORA massively accelerates NGS short-read mapping by introducing a novel approach that simultaneously exploits redundancy within read datasets and homologies in the reference genome.

CORA's read compression scheme enables massive reduction of the cost of coarse-mapping, which includes both the seed and extend stages.

The CORA framework provides for mapping NGS data (e.g., mid-size k-mer (32-63 bps), and the approach is uniquely tailored to the entropy and low fractal dimension of the data.

As a further advantage, CORA can sensitively detect indels in the alignment, provided that the coarse mapper can detect indels.

CORA is further advantageous because it produces mapping results in the same read order as the input dataset and preferably reports all mappings of a read together.

Compressing the reads and references as described herein allows CORA to scale with the amount of non-redundant data, as it can operate directly on the compressed data.

As a compressive-acceleration framework, the CORA framework utilizes redundancy within read datasets by identifying redundant k-mer sequences within read datasets and jointly representing identical k-mers as a single unit for coarse-mapping. The output of this process preferably is fed into an off-the-shelf read-mapping method that identifies matches between the reference and the compressed k-mers. While others have typically used short seeds or whole reads, CORA preferably uses longer k-mer based compression of reads for mapping. Importantly, one of CORA's major advance lies in how these k-mers are coalesced with the novel homology table for the reference, also based on k-mers which link to "neighboring" k-mers within a threshold Hamming distance.

CORA uses compression of reads to reduce the total time of coarse-mapping (mapping k-mer representatives), which includes both the seed-matching and extend stages. Through CORA's compression scheme, its coarse-mapping stage, which accounts for the bulk of the total computational cost, scales sublinearly in the read dataset size and thus represents a highly advantageous advance over existing methods, which scale linearly. In other words, the coarse-mapping stage scales linearly with the non-redundant data within read datasets and therefore sublinearly in practice for sequencing datasets. This scaling property manifests most prominently in that the relative advantage of CORA over other techniques (e.g., mrsFAST-Ultra, as well as other mapping tools) increases as coverage is increased and sequencing error rate is reduced.

The flexibility of the CORA framework enables it to adopt the functionalities of the coarse-mappers that it uses. For example, and as described, CORA can perform alignment with indels, provided that the coarse-mapper used within CORA is able to report coarse mappings with indels. If, however, the coarse-mapper is a substitution-only mapper, CORA's final results would also be limited to substitution-only mappings. Other coarse-mapper functionalities can also be easily incorporated into the CORA framework; for instance, when coarse-mapping is performed with mrsFAST-Ultra, its SNP-aware alignment algorithm, which reduces reference mapping bias, can be made available to CORA.

The described k-mer-based read compression scheme complements the homology table, as they both represent k-mers and their neighbors, allowing CORA to operate directly on the compressed k-mers from reads and discover inexact matches to the reference. A unified k-mer based framework, such as described herein, has not been previously utilized by read-mapping methods. Additionally, because the read k-mer framework naturally incorporates indels, the framework is able to do all-mapping with indels, and without the substantial loss of sensitivity and speed exhibited by other software (e.g. Masai, GEM).

The CORA framework allows the k-mer length and number of k-mers to be chosen independently from the read length. Theoretically, in terms of the asymptotic time complexity of homology table traversal (or the mapping inference stage), there is not any difference between different k-mer lengths chosen, as computations are done in edit space rather than in nucleotide space. If the number of k-mers is increased, the time complexity will only change linearly with the number of k-mers per read, though memoization would for the most part offset this change in practice. This gives a flexible and robust framework where the number of k-mers and k-mer lengths can be chosen independently from the read length, also allowing selection of overlapping k-mers and k-mers with gaps in between. The framework may support flexible k-mer selection scheme for more robust read-mapping acceleration.

As has been described, preferably CORA utilizes an off-the-shelf mapper to match compressed substrings of reads (k-mers) to the reference genome; the CORA framework itself need not specify which particular similarity search is to be used. Because in this example embodiment CORA is dependent on the off-the-shelf mapper, this search can be performed under edit distance as well as Hamming distance, depending on the capabilities of the coarse-mapper.

While the disclosed subject matter will be described in the context of a method or process, the subject matter also relates to apparatus for performing the operations herein. This apparatus may be a particular machine that is specially constructed for the required purposes, or it may comprise a computer otherwise selectively activated or reconfigured by a computer program stored in the computer. Such a computer program may be stored in a computer readable storage medium, such as, but is not limited to, any type of disk including an optical disk, a CD-ROM, and a magnetic-optical disk, a read-only memory (ROM), a random access memory (RAM), a magnetic or optical card, or any type of media suitable for storing electronic instructions, and each coupled to a computer system bus. A given implementation of the disclosure is software written in a given programming language that runs in conjunction with a proxy on a standard Intel hardware platform running an operating system such as Linux. The functionality may be built into other code, or it may be executed as an adjunct to that code. A machine implementing the techniques herein comprises a processor, computer memory holding instructions that are executed by the processor to perform the above-described methods, functions or operations. Functions described herein may be implemented across multiple machines, processes, programs, systems and the like, co-located or remote from one another.

While given components of the system have been described separately, one of ordinary skill will appreciate that some of the functions may be combined or shared in given instructions, program sequences, code portions, and the like.

Processing (computation, storage or otherwise) as described herein may be implemented in whole or in part using cloud computing. As is well-known, cloud computing is a model of service delivery for enabling on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. Available services models that may be leveraged in whole or in part include: Software as a Service (SaaS) (the provider's applications running on cloud infrastructure); Platform as a service (PaaS) (the customer deploys applications that may be created using provider tools onto the cloud infrastructure); Infrastructure as a Service (IaaS) (customer provisions its own processing, storage, networks and other computing resources and can deploy and run operating systems and applications).

A cloud platform may comprise co-located hardware and software resources, or resources that are physically, logically, virtually and/or geographically distinct. Communication networks used to communicate to and from the platform services may be packet-based, non-packet based, and secure or non-secure, or some combination thereof.

The techniques herein provide for improvements to another technology or technical field, namely, next-generation sequencing (NGS), as well as improvements to the functioning of compression techniques.

Having described the above-described subject matter, what is claimed follows below.

The invention claimed is:

1. A method of accelerating processing of a dataset of data, comprising:
during a first phase:
generating a table for a reference sequence, the table storing similarity information of similar regions of the reference sequence of a specified length within a given distance;
during a second phase that is distinct from the first phase:
compressing given information in the dataset to generate compressed data;
applying a coarse mapping from the compressed data to the reference sequence to generate a set of links, each link being a pointer to the table and representing a cluster of substrings from the given information in the dataset;
processing the set of links through traversal of the table to obtain a mapping result set; and
recovering one or more mappings that are missed during traversal of the table to generate a final mapping result set;
wherein processing the set of links using the table provides sublinear-time mapping of the dataset and without requiring decompression of the compressed data.

2. The method as described in claim 1 wherein the set of links are processed in a multi-pass computation.

3. The method as described in claim 1 wherein the table is a homology table that is a layered structure, wherein commonly-accessed homologies are stored in memory and a remainder are stored on disk.

4. The method as described in claim 1 wherein the data is genomic data and the given information are reads.

5. The method as described in claim 1 wherein the reference sequence is a reference genomic sequence and the table is a homology table that contains homologous pairs of loci in the reference genomic sequence for a given homology block length and above a similarity threshold.

6. The method as described in claim 1 wherein the table is a homology table, and the homology table is selected from homology tables of common reference genomes for a variety of k-mer lengths.

7. The method as described in claim 1 wherein the coarse mapper is one of: a substitution mapper, and an insertion and deletion mapper.

* * * * *